US010973600B2

(12) United States Patent
Bruehwiler et al.

(10) Patent No.: US 10,973,600 B2
(45) Date of Patent: Apr. 13, 2021

(54) POWER AXLE WRIST FOR ROBOTIC SURGICAL TOOL

(71) Applicant: Ethicon LLC, Guaynabo, PR (US)

(72) Inventors: Michel Bruehwiler, Newton, MA (US); Cole Constantineau, Cambridge, MA (US); Andrew Ryan, Boston, MA (US); Khodabakhsh Saeedi, Cambridge, MA (US)

(73) Assignee: ETHICON LLC, Guaynabo, PR (US)

( * ) Notice: Subject to any disclaimer, the term of this patent is extended or adjusted under 35 U.S.C. 154(b) by 440 days.

(21) Appl. No.: 15/720,699

(22) Filed: Sep. 29, 2017

(65) Prior Publication Data

US 2019/0099231 A1 Apr. 4, 2019

(51) Int. Cl.
*A61B 34/00* (2016.01)
*B25J 17/02* (2006.01)
(Continued)

(52) U.S. Cl.
CPC .............. *A61B 34/71* (2016.02); *A61B 10/04* (2013.01); *A61B 17/00234* (2013.01); *A61B 17/29* (2013.01); *A61B 34/30* (2016.02); *B25J 17/02* (2013.01); *A61B 1/012* (2013.01); *A61B 2017/2926* (2013.01);
(Continued)

(58) Field of Classification Search
CPC ......... A61B 34/71; A61B 17/29; A61B 34/30; A61B 17/00234; A61B 10/04; A61B 2017/2927; A61B 2017/2926; A61B 2034/302; A61B 2034/305; B25J 17/02
See application file for complete search history.

(56) References Cited

U.S. PATENT DOCUMENTS 7,854,738 B2 12/2010 Lee et al.
8,831,782 B2 9/2014 Itkowitz
(Continued)

FOREIGN PATENT DOCUMENTS

| WO | 2014/151621 | 9/2014 |
|---|---|---|
| WO | 2014/151952 | 9/2014 |
| WO | 2015088647 A1 | 6/2015 |

OTHER PUBLICATIONS

ISRWO of corresponding PCT/IB2018/057304 with mail date of Dec. 17, 2018.
(Continued)

*Primary Examiner* — Thomas McEvoy
(74) *Attorney, Agent, or Firm* — Vorys, Sater, Seymour and Pease LLP

(57) ABSTRACT

A surgical tool includes a drive housing and an elongate shaft extending from the drive housing. A wrist couples an end effector to the elongate shaft and includes a distal clevis having a first axle that rotatably mounts the end effector to the distal clevis, and a proximal clevis coupled to the elongate shaft and having a second axle that rotatably mounts the distal clevis to the proximal clevis. A plurality of drive cables extend between the drive housing and the end effector, and movement of the drive cables causes the end effector to articulate about a first pivot axis extending through the first axle. A power axle cable extending from the drive housing and mounted to the distal clevis such that movement of the power axle cable correspondingly pivots the end effector about a second pivot axis at the second axle.

19 Claims, 7 Drawing Sheets

(51) Int. Cl.
*A61B 34/30* (2016.01)
*A61B 17/29* (2006.01)
*A61B 10/04* (2006.01)
*A61B 17/00* (2006.01)
*A61B 1/012* (2006.01)

(52) U.S. Cl.
CPC . *A61B 2017/2927* (2013.01); *A61B 2034/302* (2016.02); *A61B 2034/305* (2016.02)

(56) References Cited

U.S. PATENT DOCUMENTS

| | | |
|---|---|---|
| 2004/0266574 A1 | 12/2004 | Jinno et al. |
| 2007/0255109 A1 | 11/2007 | Stein et al. |
| 2008/0119870 A1 | 5/2008 | Williams |
| 2011/0071543 A1* | 3/2011 | Prisco .................... A61B 34/76 606/130 |
| 2015/0313676 A1 | 11/2015 | Deodhar |
| 2015/0313678 A1 | 11/2015 | Park et al. |
| 2016/0287252 A1 | 10/2016 | Parihar |
| 2017/0165017 A1 | 6/2017 | Chaplin et al. |

OTHER PUBLICATIONS

EP Search Report for corresponding EP application No. EP18197703 dated Feb. 12, 2019.

* cited by examiner

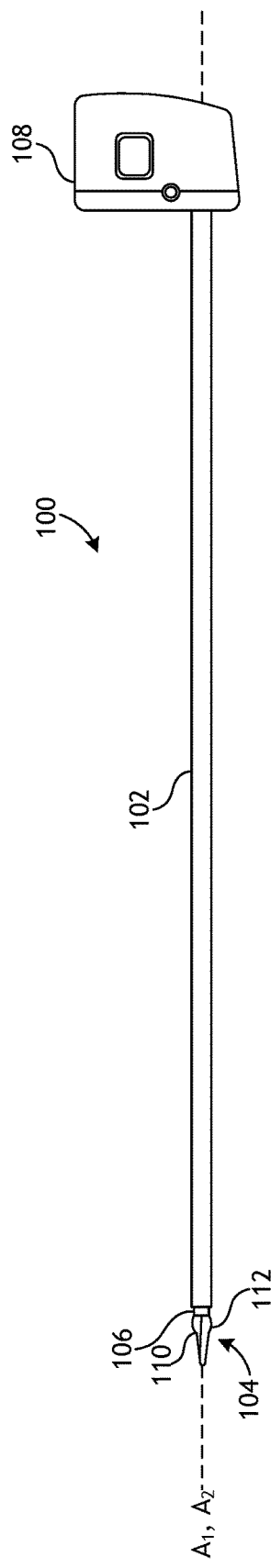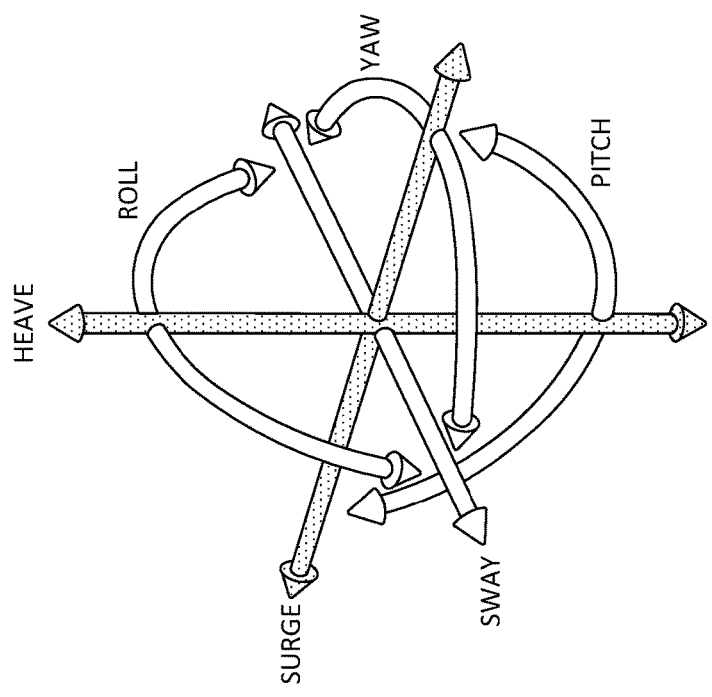
FIG. 1
FIG. 2

POWER AXLE WRIST FOR ROBOTIC SURGICAL TOOL

BACKGROUND

Minimally invasive surgical (MIS) instruments are often preferred over traditional open surgical devices due to reduced post-operative recovery time and minimized scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint on the instrument, which creates a more natural hand-like articulation.

To facilitate operation of the wrist joint, robotic systems typically include cable driven motion systems designed to articulate (move) the instrument's end effector. Common cable driven motion system include one or more drive cables (alternately referred to as elongate members or wires) that extend through the wrist joint to aid in articulating the instrument's end effector. Some surgical tools, such as needle drivers and graspers (forceps), require large amounts of grip force and higher load capacity to properly undertake various surgical procedures. Conventional cable driven motion systems often cannot provide the sufficient grip force and load capacity required to undertake these various surgical procedures.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 1 is a side view of an example surgical tool that may incorporate some or all of the principles of the present disclosure.

FIG. 2 illustrates potential degrees of freedom in which the wrist of FIG. 1 may be able to articulate (pivot).

DETAILED DESCRIPTION

Figure 3:
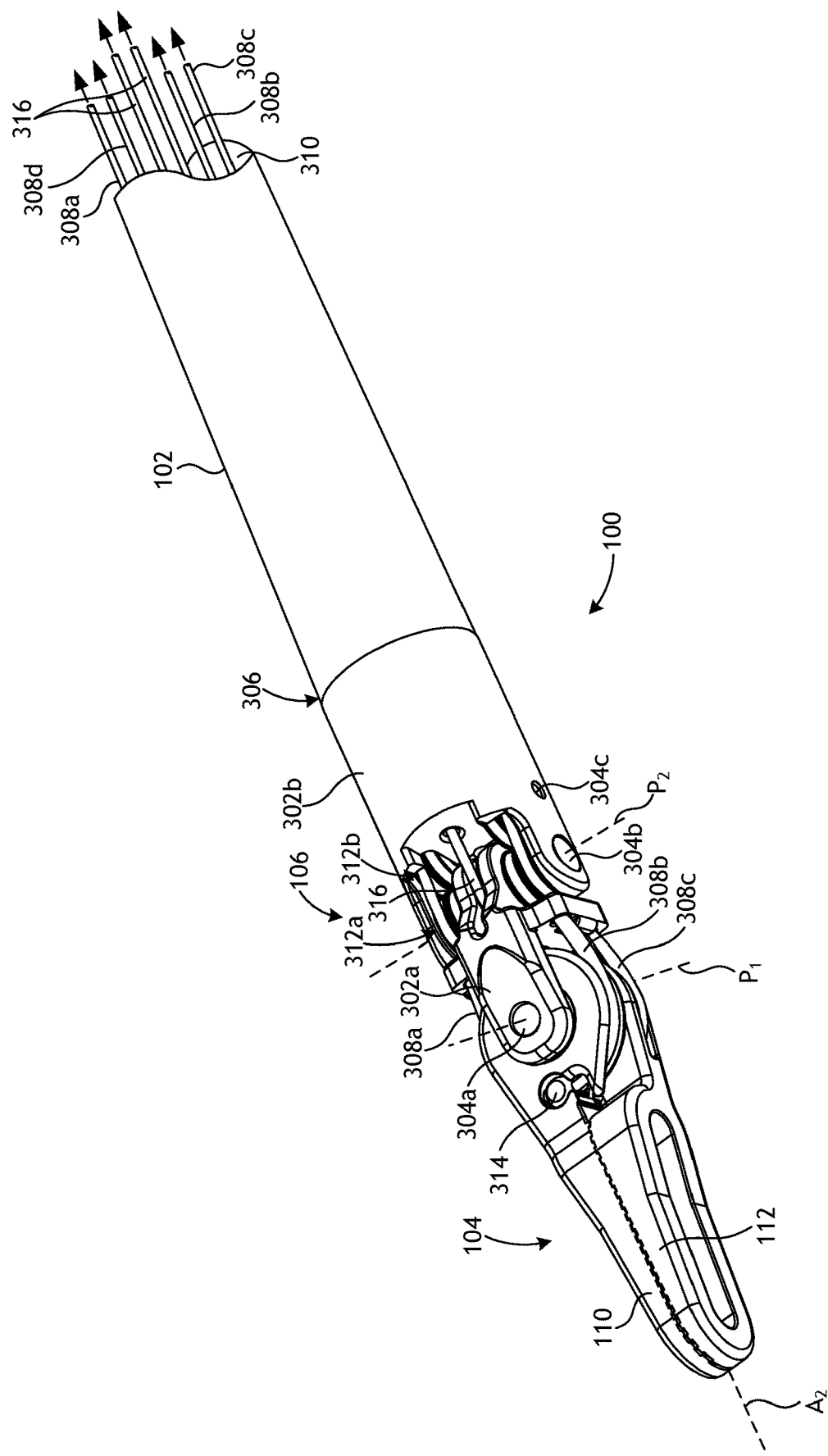
FIG. 3 is an enlarged isometric view of the distal end of the surgical tool of FIG. 1.

The present disclosure is related to robotic surgery systems and, more particularly, to robotic surgical tools having a wrist joint that incorporates a power axle cable that delivers elevated force to the wrist joint and an associated end effector.

The embodiments disclosed herein describe a power axle wrist for a robotic surgical tool. The surgical tool includes a drive housing and an elongate shaft extending from the drive housing. The power axle wrist couples an end effector to the elongate shaft and includes a distal clevis having a first axle that rotatably mounts the end effector to the distal clevis, and a proximal clevis coupled to the elongate shaft and having a second axle that rotatably mounts the distal clevis to the proximal clevis. A plurality of drive cables extend between the drive housing and the end effector, and movement of the drive cables causes the end effector to articulate about a first pivot axis extending through the first axle. A power axle cable extends from the drive housing and is mounted to the distal clevis such that movement of the power axle cable correspondingly pivots the end effector about a second pivot axis at the second axle. The power axle cable is dedicated entirely to transmitting force to the distal clevis and thereby provides an elevated amount of force and loading capability for the end effector.

FIG. 1 is side view of an example surgical tool 100 that may incorporate some or all of the principles of the present disclosure. As illustrated, the surgical tool 100 includes an elongate shaft 102, an end effector 104, a wrist 106 (alternately referred to as a "wrist joint") that couples the end effector 104 to the distal end of the shaft 102, and a drive housing 108 coupled to the proximal end of the shaft 102. In at least some embodiments, the surgical tool 100 may be designed to be releasably coupled to a robotic surgical system, and the drive housing 108 can include coupling features that releasably couple the surgical tool 100 to the robotic surgical system.

The terms "proximal" and "distal" are defined herein relative to a robotic surgical system having an interface configured to mechanically and electrically couple the surgical tool 100 (e.g., the housing 108) to a robotic manipulator. The term "proximal" refers to the position of an element closer to the robotic manipulator and the term "distal" refers to the position of an element closer to the end effector 104 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 100, the end effector 104 is configured to move (pivot) relative to the shaft 102 at the wrist 106 to position the end effector 104 at a desired orientation and location relative to a surgical site. The housing 108 includes various mechanisms designed to control operation of various features associated with the end effector 104 (e.g., clamping, firing, rotation, articulation, energy delivery, etc.). In at least some embodiments, the shaft 102, and hence the end effector 104 coupled thereto, is configured to rotate about a longitudinal axis $A_1$ of the shaft 102. In such embodiments, at least one of the mechanisms included in the housing 108 is configured to control rotational movement of the shaft 102 about the longitudinal axis $A_1$.

The surgical tool 100 can have any of a variety of configurations capable of performing at least one surgical function. For example, the surgical tool 100 may include, but is not limited to, forceps, a grasper, a needle driver, scissors, an electro cautery tool, a stapler, a clip applier, a suction tool, an irrigation tool, an imaging device (e.g., an endoscope or ultrasonic probe), or any combination thereof. In some embodiments, the surgical tool 100 may be configured to apply energy to tissue, such as radiofrequency (RF) energy.

The shaft 102 is an elongate member extending distally from the housing 108 and has at least one lumen extending therethrough along its axial length. In some embodiments, the shaft 102 may be fixed to the housing 108, but could alternatively be rotatably mounted to the housing 108 to allow the shaft 102 to rotate about the longitudinal axis $A_1$. In yet other embodiments, the shaft 102 may be releasably coupled to the housing 108, which may allow a single housing 108 to be adaptable to various shafts having different end effectors.

The end effector 104 can have a variety of sizes, shapes, and configurations. In the illustrated embodiment, the end effector 104 comprises a tissue grasper having opposing jaws 110, 112 configured to move between open and closed positions. One or both of the jaws 110, 112 may be configured to pivot at the wrist 106 to move the end effector 104 between the open and closed positions. In other embodiments, however, the end effector 104 may have other configurations, e.g., scissors including a pair of opposed cutting blades, a babcock including a pair of opposed grasping jaws, a retractor, a hook, a spatula, needle drivers, graspers, forceps, etc.

The wrist 106 can have any of a variety of configurations. In general, the wrist 106 comprises a joint configured to allow pivoting movement of the end effector 104 relative to the shaft 102. According to embodiments of the present disclosure, and as discussed in more detail below, the wrist 106 may be characterized as a "Power Axle Wrist" capable of delivering elevated force and loading to the end effector 104 as compared to conventional wrist joints.

FIG. 2 illustrates the potential degrees of freedom in which the wrist 106 may be able to articulate (pivot). The degrees of freedom of the wrist 106 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 104) with respect to a given reference Cartesian frame. As depicted in FIG. 2, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 106 (e.g., X-axis), yaw movement about a second axis of the wrist 106 (e.g., Y-axis), and combinations thereof to allow for 360° rotational movement of the end effector 104 about the wrist 106. In other applications, the pivoting motion can be limited to movement in a single plane, e.g., only pitch movement about the first axis of the wrist 106 or only yaw movement about the second axis of the wrist 106, such that the end effector 104 moves only in a single plane.

Referring again to FIG. 1, the surgical tool 100 includes a plurality of drive cables (obscured in FIG. 1) that form part of a cable driven motion system configured to effect movement (pivoting) of the end effector 104 relative to the shaft 102. The drive cables may be referred to and otherwise characterized as cables, bands, lines, cords, wires, ropes, strings, twisted strings, elongate members, etc. The drive cables can be made from a variety of materials including, but not limited to, metal (e.g., tungsten, stainless steel, etc.) or a polymer. Example drive cables are described in U.S. Patent Pub. No. 2015/0209965 entitled "Compact Robotic Wrist," and U.S. Patent Pub. No. 2015/0025549 entitled "Hyperdexterous Surgical System", the contents of which are hereby incorporated by reference.

The drive cables are operably coupled to various actuation mechanisms housed within the drive housing 108 and extend within the lumen of the shaft 102 to the wrist 106 where they are operably engaged with the end effector 104. Selective actuation of all or a portion of the drive cables causes the end effector 104 (e.g., one or both of the jaws 110, 112) to move (pivot) relative to the shaft 102. More specifically, selective actuation causes a corresponding drive cable to translate longitudinally within the lumen of the shaft 102 and thereby cause pivoting movement of the end effector 104. In operation, one or more drive cables may translate longitudinally to cause the end effector 104 to articulate (e.g., both of the jaws 110, 112 angle in a same direction), to cause the end effector 104 to open (e.g., one or both of the jaws 110, 112 move away from the other), or to cause the end effector 104 to close (e.g., one or both of the jaws 110, 112 move toward the other).

Actuation of the drive cables can be accomplished in a variety of ways, such as by triggering an associated actuator operably coupled to or housed within the drive housing 108. Actuation applies tension to (i.e., pulls) the drive cables in a proximal direction to cause the corresponding elongate member to translate and thereby cause the end effector 104 to move (articulate) relative to the shaft 102. When both of the jaws 110, 112 are designed to move to open and close the end effector 104, one or more first drive cables will be operably coupled to the first jaw 110 to move that jaw 110 and one or more second drive cables will be operably coupled to the second jaw 112 to move that jaw 112. When only one of the jaws 110, 112 is configured to move to open and close the end effector 104, one or more drive cables may be operably coupled to the first jaw 110 to move the first jaw 110 relative to the second jaw 112.

Actuating the drive cables moves the end effector 104 between an unarticulated position and an articulated position. The end effector 104 is depicted in FIG. 1 in the unarticulated position where a longitudinal axis $A_2$ of the end effector 104 is substantially aligned with the longitudinal axis $A_1$ of the shaft 102, such that the end effector 104 is at a substantially zero angle relative to the shaft 102. Due factors such as manufacturing tolerance and precision of measurement devices, the end effector 104 may not be at a precise zero angle relative to the shaft 102 in the unarticulated position, but nevertheless be considered "substantially aligned" thereto. In the articulated position, the longitudinal axes $A_1$, $A_2$ would be angularly offset from each other such that the end effector 104 is at a non-zero angle relative to the shaft 102.

The drive housing 108 (alternately referred to as a "puck") may be releasably latched (attached) to a tool driver of a robotic surgical system in a variety of ways, such as by clamping thereto, clipping thereto, or slidably mating therewith. The actuation devices or mechanisms housed within the drive housing 108 may be controlled by the robot based on user inputs received via a computer system incorporated into the robot. Accordingly, the user inputs control movement of the drive cables and consequently movement of the end effector 104.

Example tool drivers to which the drive housing 108 may be removably attached are described in previously mentioned U.S. patent application Ser. No. 15/200,283. Moreover, the drive housing 108 illustrated in FIG. 1 is but one example of a suitable drive housing, and additional embodiments of the drive housing 108 are described in previously mentioned U.S. Patent Pub. Nos. 2015/0209965 and 2015/0025549. Example robotic surgical systems are described in U.S. Pat. No. 8,831,782 entitled "Patient-Side Surgeon Interface for a Teleoperated Surgical Instrument" and previously mentioned U.S. Patent Pub. Nos. 2015/0209965 and 2015/0025549.

FIG. 3 is an enlarged isometric view of the distal end of the surgical tool 100 of FIG. 1. More specifically, FIG. 3 depicts enlarged views of the end effector 104 and the wrist 106, with the end effector 104 in the unarticulated position where the jaws 110, 112 are closed. The wrist 106 operatively couples the end effector 104 to the shaft 102. To accomplish this, the wrist 106 includes a distal clevis 302a and a proximal clevis 302b. The end effector 104 (i.e., the jaws 110, 112) is rotatably mounted to the distal clevis 302a at a first axle 304a, the distal clevis 302a is rotatably mounted to the proximal clevis 302b at a second axle 304b, and the proximal clevis 302b is coupled to a distal end 306 of the shaft 102.

The wrist 106 provides a first pivot axis $P_1$ that extends through the first axle 304a and a second pivot axis $P_2$ that extends through the second axle 304b. The first pivot axis $P_1$ is substantially perpendicular (orthogonal) to the longitudinal axis $A_2$ of the end effector 104, and the second pivot axis $P_2$ is substantially perpendicular to both the longitudinal axis $A_2$ and the first pivot axis $P_1$. Movement about the first pivot axis $P_1$ provides "yaw" articulation of the end effector 104, and movement about the second pivot axis $P_2$ provides "pitch" articulation of the end effector 104. In the illustrated embodiment, the jaws 110, 112 are mounted at the first pivot axis $P_1$, thereby allowing the jaws 110, 112 to pivot relative to each other to open and close the end effector 104 or alternatively pivot in tandem to articulate the orientation of the end effector 104.

A plurality of drive cables 308, shown as drive cables 308a, 308b, 308c, and 308d, extend longitudinally within a lumen 310 of the shaft 102 until terminating at the wrist 106. The drive cables 308a-d extend proximally from the end effector 104 to the drive housing 108 (FIG. 1) which, as discussed above, may be configured to facilitate longitudinal movement of the drive cables 308a-d within the lumen 310. The lumen 310 can be a single lumen, as illustrated, or can alternatively comprise a plurality of independent lumens that each receive one or more of the drive cables 308a-d.

The wrist 106 includes a first plurality of pulleys 312a and a second plurality of pulleys 312b each configured to interact with and redirect the drive cables 308a-d for engagement with the end effector 104. The first plurality of pulleys 312a is mounted to the proximal clevis 302b at the second axle 304b and the second plurality of pulleys 312b is mounted to the proximal clevis 302b at a third axle 304c. The third axle 304c is located proximal to the second axle 304b. The first and second plurality of pulleys 312a,b cooperatively redirect the drive cables 308a-d through an "S" shaped pathway.

In at least one embodiment, one pair of drive cables 308a-d is operatively coupled to each jaw 110, 112 and configured to "antagonistically" operate the corresponding jaw 110, 112. In the illustrated embodiment, for example, the first and second drive cables 308a,b are coupled at a connector 314 mounted to the first jaw 110, and the third and fourth drive cables 308c,d are coupled at another connector (hidden in FIG. 3) mounted to the second jaw 112. Actuation of the first drive cable 308a acts on the connector 314 and thereby pivots the first jaw 110 about the first pivot axis $P_1$ toward the open position. In contrast, actuation of the second drive cable 308b acts on the connector 314 and thereby pivots the first jaw 110 about the first pivot axis $P_1$ in the opposite direction and toward the closed position. Similarly, actuation of the third drive cable 308c acts on the corresponding connector (not shown) and thereby pivots the second jaw 112 about the first pivot axis $P_1$ toward the open position, while actuation of the fourth drive cable 308d acts on the corresponding connector to pivot the second jaw 112 about the first pivot axis $P_1$ in the opposite direction and toward the closed position.

Accordingly, the drive cables 308a-d may be characterized or otherwise referred to as "antagonistic" cables that cooperatively (antagonistically) operate to cause relative or tandem movement of the first and second jaws 110, 112. When the first drive cable 308a is actuated, the second drive cable 308b naturally follows as coupled to the first drive cable 308a at the connector 314, and vice versa. Similarly, when the third drive cable 308c is actuated, the fourth drive cable 308d naturally follows as coupled to the third drive cable 308c at the other connector (hidden in FIG. 3), and vice versa.

Moreover, coordinated actuation of the drive cables 308a-d may also articulate the end effector 104 about the second pivot axis $P_2$. Consequently, the end effector 104 can articulate with multiple degrees of freedom, e.g., a degree of freedom by articulating about the first pivot axis $P_1$ and another degree of freedom by articulating about the second pivot axis $P_2$. The wrist 106 in this embodiment is pivotable about the second pivot axis $P_2$ in a single plane, e.g., in one of pitch and yaw, and the end effector 104 is pivotable about the first pivot axis $P_1$ in a single, different plane, e.g., the other of pitch and yaw.

According to the present disclosure, the tool 100 may further include a power axle cable 316, also extending longitudinally within the lumen 310 until terminating at the wrist 106 where the distal and proximal clevises 302a,b are coupled. Similar to the drive cables 308a-d, the power axle cable 316 extends from the drive housing 108 (FIG. 1), which houses one or more actuation mechanisms used to selectively actuate the power axle cable 316 and thereby facilitate longitudinal movement (translation) of the power axle cable 316 within the lumen 310. In some embodiments, the power axle cable 316 is a closed loop cable that interfaces with only one actuation mechanism in the drive housing 108. In other embodiments, however, the power axle cable 316 may comprise two power axle cables coupled at the distal clevis 302a and each interfacing with an independent mechanism in the drive housing 108, without departing from the scope of the disclosure.

The power axle cable 316 is dedicated to transmitting force to the distal clevis 302a, which provides elevated force and load capabilities to the end effector 104. In operation, actuation of the power axle cable 316 in a first direction pivots the distal clevis 302a, and therefore the end effector 104, about the second pivot axis $P_2$ in a first "pitch" direction. In contrast, actuation of the power axle cable 316 in a second direction opposite the first direction pivots the distal clevis 302a (and the end effector 104) about the second pivot axis $P_2$ in a second "pitch" direction opposite the first pitch direction. As the end effector 104 moves in the first and second pitch directions, added force and load is provided to the end effector 104, which enhances its capabilities. This elevated force allows for instruments to be used to retract and grasp large organs or tissues, and to suture and manipulate a needle through thick tissue.

Figure 4:
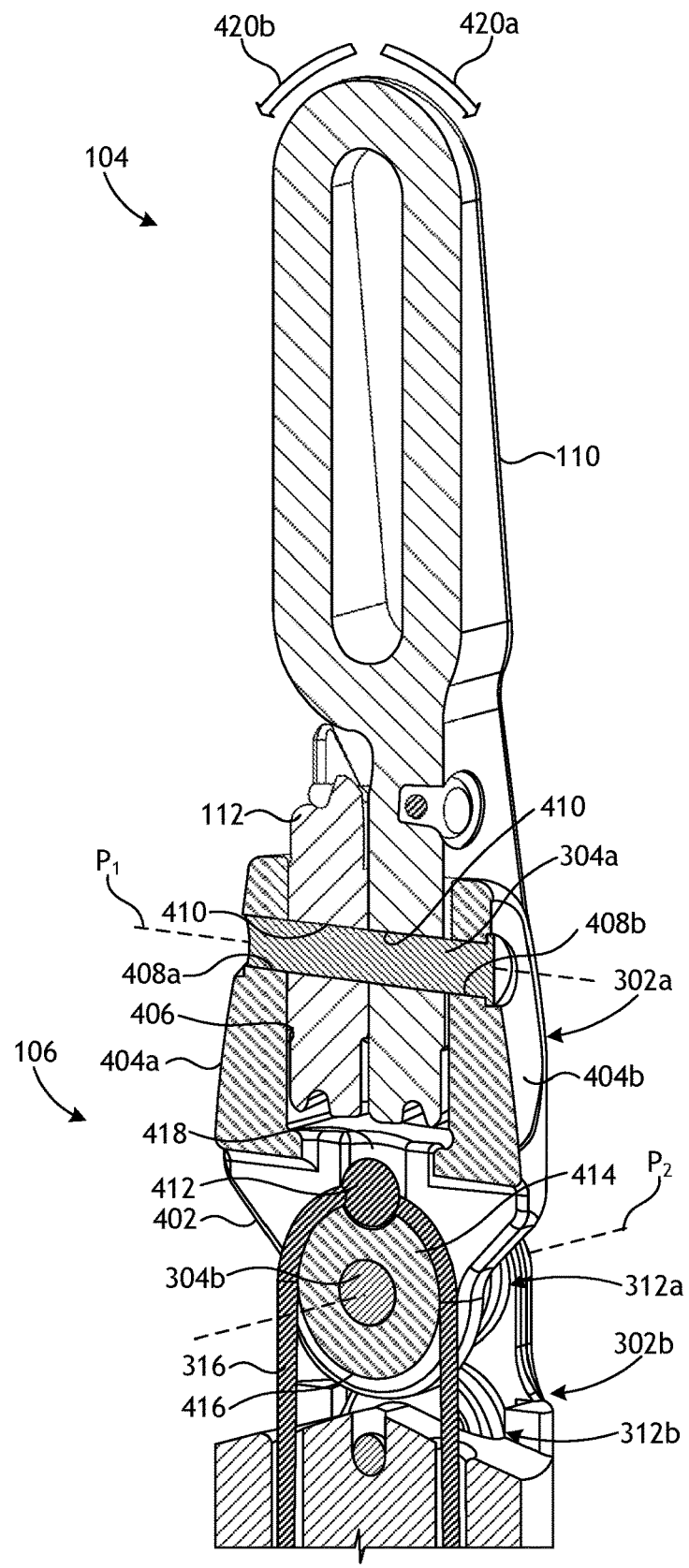
FIG. 4 is an enlarged cross-sectional side view of the wrist and the end effector of FIG. 3.

FIG. 4 is an enlarged cross-sectional side view of the wrist 106 and the end effector 104 of FIG. 3, according to one or more embodiments of the present disclosure. As illustrated and mentioned above, the end effector 104 is rotatably mounted to the distal clevis 302a at the first axle 304a, and the distal clevis 302a is rotatably mounted to the proximal clevis 302b at the second axle 304b.

The distal clevis 302a comprises a body 402 that provides and otherwise defines a first extension 404a and a second extension 404b laterally offset from the first extension 404a. A cavity 406 is defined between the first and second extensions 404a,b and configured to receive a portion of the end effector 104. In the illustrated embodiment, for example, the cavity 406 is sized to receive a proximal portion of each of the first and second jaws 110, 112.

To secure the end effector 104 to the distal clevis 302a, the first axle 304a is extendable through first and second holes 408a, 408b defined by the first and second extensions 404a,b, respectively. The first axle 304a is also extendable through corresponding holes 410 defined by the end effector 104 (i.e., through proximal portions of each jaw 110, 112). Once mounted to the first axle 304a, the end effector 104 is capable of rotating about the first pivot axis $P_1$ as acted upon by the corresponding drive cables 308a-d (FIG. 3).

As illustrated, a power axle connector 412 may be used to mount the power axle cable 316 to the distal clevis 302a. The distal clevis 302a may provide an inner pulley 414 defining an inner groove 416 that concentrically circumscribes the second axle 304b. The power axle cable 316 may be received within the inner groove 416 and thereby routed concentrically around the second axle 304b, and the power axle connector 412 holds the power axle cable 316 in place on the distal clevis 302a.

The power axle connector 412 may comprise any attachment mechanism capable of mounting the power axle cable 316 to the distal clevis 302a such that movement (actuation) of the power axle cable 316 on one side of the power axle connector 412 correspondingly moves the power axle cable 316 on the opposing side of the power axle connector 412. In the illustrated embodiment, for example, the power axle connector 412 may comprise a crimp, such as a ball crimp. Other types of crimps may alternatively be employed including, but not limited to, a barrel crimp, a double barrel crimp, etc. In other embodiments, however, the power axle connector 412 may alternatively comprise a welded attachment, a brazed attachment, an adhesive bond, a mechanical fastener, and any combination thereof.

The power axle connector 412 may be mounted to the distal clevis 302a by being received within a pocket 418 defined by the distal clevis 302a. The pocket 418 may be sized such that, when the power axle connector 412 is received therein, movement of the power axle cable 316 causes the power axle connector 412 to act on and urge the distal clevis 302a to move about the second pivot axis $P_2$.

Movement (actuation) of the power axle cable 316 in a first direction, for example, will move (rotate) the distal clevis 302a about the second pivot axis $P_2$ in a first or "clockwise" direction 420a. In contrast, movement (actuation) of the power axle cable 316 in a second direction opposite the first direction will move (rotate) the distal clevis 302a about the second pivot axis $P_2$ in a second or "counterclockwise" direction 420b. Moreover, since the end effector 104 is coupled to the distal clevis 302a at the first axle 304a, movement of the power axle cable 316 will correspondingly pivot the end effector 104 about the second pivot axis $P_2$ in the same direction.

The power axle cable 316 is dedicated entirely to transmitting force to the distal clevis 302a. Unlike the drive cables 308a,b (FIG. 3), which are routed around the first and second pluralities of pulleys 312a,b, the power axle cable 316 is routed directly to the distal clevis 302a. Routing the drive cables 308a,b around the first and second pluralities of pulleys 312a,b introduces friction and reduces available load capacity. Since the power axle cable 316 is directly routed to the distal clevis 302a, greater force and loading capability for the end effector 104 is available.

Figure 5:
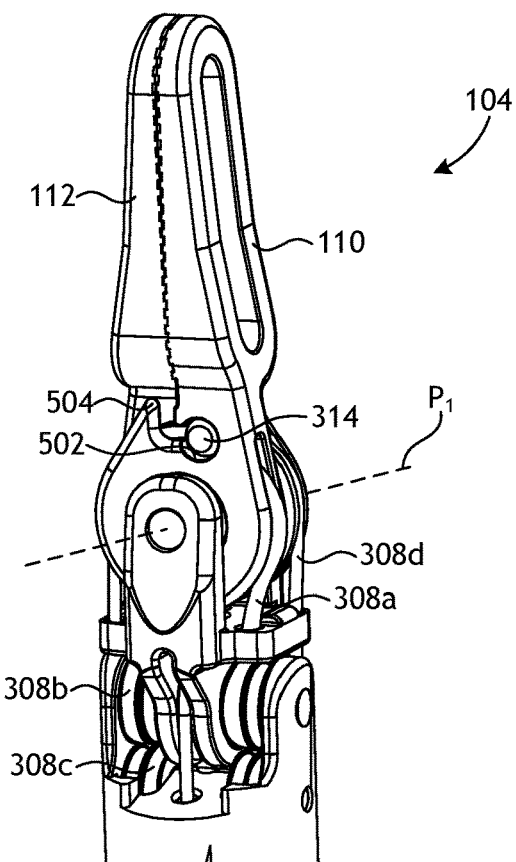
FIG. 5 is an enlarged isometric view of the end effector of FIG. 3.

FIG. 5 is an isometric side view of the end effector 104, according to one or more embodiments. Again, the illustrated end effector 104 includes opposing first and second jaws 110, 112 and is movable between open and closed positions as acted upon by the drive cables 308a-d. Moreover, the first and second drive cables 308a,b are coupled at the connector 314, which is mounted to the first jaw 110, and the third and fourth drive cables 308c,d are coupled at another connector (hidden in FIG. 5), which is mounted to the second jaw 112.

The connector 314 (and the hidden connector) may comprise any attachment mechanism capable of coupling the corresponding drive cables 308a-d such that movement (actuation) of one drive cable correspondingly moves the other associated drive cable, and vice versa. In the illustrated embodiment, for example, the connector 314 (and the hidden connector) may comprise a ball crimp. In other embodiments, however, the connector 314 (and the hidden connector) may comprise any of the attachment mechanisms mentioned herein with reference to the power axle connector 412 of FIG. 4.

As illustrated, the connector 314 may be received within a pocket 502 defined by the first jaw 110. While not visible in FIG. 5, the hidden connector mounted to the second jaw 112 may likewise be received within a corresponding pocket defined by the second jaw 112. For purposes of the disclosure, only the visible connector 314 and pocket 502 will be discussed, but it will be appreciated that the discussion may equally apply to the hidden connector and pocket of the second jaw 112, without departing from the scope of the disclosure.

The pocket 502 may be sized to receive the connector 314 such that movement of the first drive cable 308a correspondingly moves the second drive cable 308b, and vice versa, but also simultaneously urges the connector 314 to act on the first jaw 110 to move about the first pivot axis $P_1$. In some embodiments, the end effector 104 may further provide a nose 504 that helps the first drive cable 308a maintain its position and prevent the first drive cable 308a from "jumping" or slipping out of place while under full yaw articulation. In the illustrated embodiment, the nose 504 is an integral extension of the jaw 110 and extends therefrom in a direction that essentially traps and stops the connector 314 if the connector 314 is urged to escape from the pocket 502.

Figure 6:
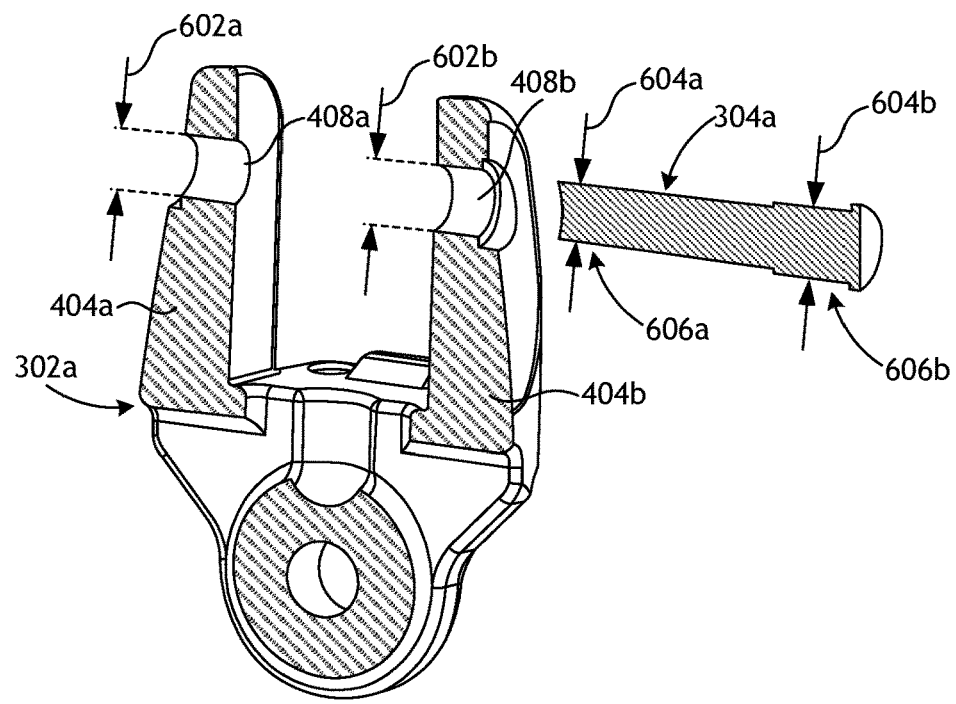
FIG. 6 is a cross-sectional side view of the distal clevis and first axle of the wrist in FIG. 3.

FIG. 6 is a cross-sectional side view of the distal clevis 302a and the first axle 304a of the wrist 106 of FIGS. 3 and 4. In some embodiments, the first hole 408a defined by the first extension 404a may have a first inner diameter 602a and the second hole 408b defined by the second extension 404b may have a second inner diameter 602b greater than the first inner diameter 412a. Moreover, the first axle 304a may be configured and otherwise sized to mate with the first and second holes 408a,b in a press-fit or shrink fit arrangement. Accordingly, the first axle 304a may exhibit a first outer diameter 604a at a first end 606a and a second outer diameter 604b at a second end 606b, where the second outer diameter 604b is greater than the first outer diameter 604a. The first inner diameter 602a may be sized to receive the first outer diameter 604a, and the second inner diameter 602b may be sized to receive the second outer diameter 604b. As will be appreciated, this may prove advantageous in accommodating easy assembly as the first axle 304a will not encounter friction until just prior to both ends 606a,b being press-fit into place into the corresponding holes 408a,b.

Figure 7:
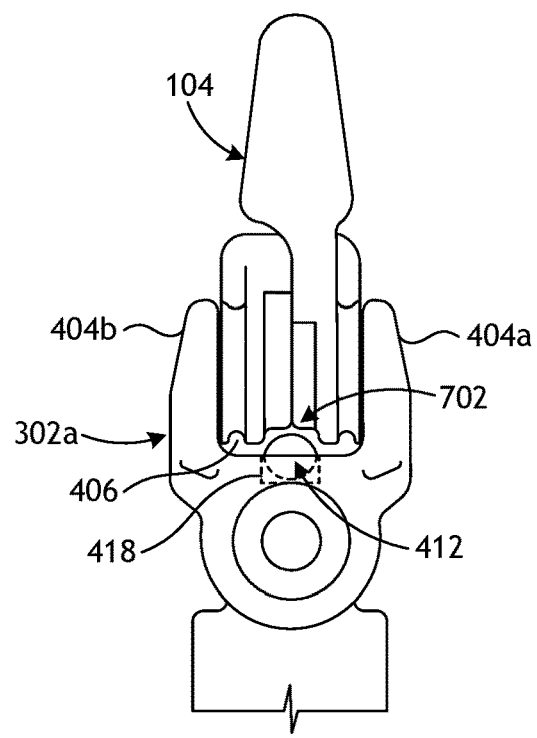
FIG. 7 is a side view of an example embodiment of the end effector of FIG. 3.

FIG. 7 is a side view of an example embodiment of the end effector 104 of FIG. 3, according to one or more additional embodiments. In the illustrated embodiment, the power axle connector 412 is seated within the pocket 418 defined in the distal clevis 302a and protrudes partially out of the pocket 418 and into the cavity 406 defined between the first and second extensions 404a,b. The power axle connector 412, however, does not interfere with articulation of the end effector 104 due to a recess 702 defined on the bottom (proximal portion) of the end effector 104. As illustrated, the recess 702 may be sized to accommodate the portion of the power axle connector 412 protruding from the pocket 418 such that the power axle connector 412 does not obstruct movement of the end effector.

Figure 8:
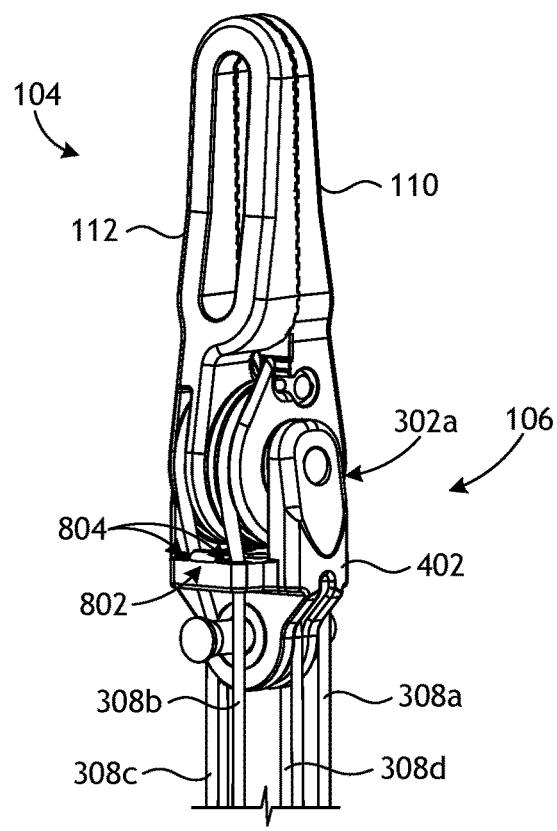
FIG. 8 is an isometric side view of the end effector and a portion of the wrist of FIGS. 3 and 4.

FIG. 8 is an isometric side view of the end effector 104 and a portion of the wrist 106 of FIGS. 3 and 4, according to one or more additional embodiments. As illustrated, the body 402 of the distal clevis 302a may define two hard stops 802 (one shown and one hidden) and a plurality of channels 804 (two shown and two hidden). Each hard stop 802 may comprise a projection defined on the body 402 and positioned to limit "yaw" movement of the corresponding jaw 110, 112 to a predetermined maximum angle. In the illustrated embodiment, the hard stop 802 is configured to stop yaw articulation of the second jaw 112, while the hidden hard stop on the opposite side of the end effector 104 is configured to stop yaw articulation of the first jaw 110. In some embodiments, the predetermined maximum angle may be about 100°, but could alternatively be more or less than 100°, without departing from the scope of the disclosure.

The plurality of channels 804 may be configured to receive the drive cables 308a-d extending proximally from the end effector 104 on each side thereof. In the illustrated embodiment, the second and third drive cables 308b,c are shown extending through the two visible channels 804, while the first and fourth drive cables 308a,d extend through two hidden channels on the opposite side of the body 402. The channels 802 are sized such that, under normal conditions, the drive cables 308a-d do not engage the channels 802 and, therefore, do not introduce friction into the system.

Figure 9:
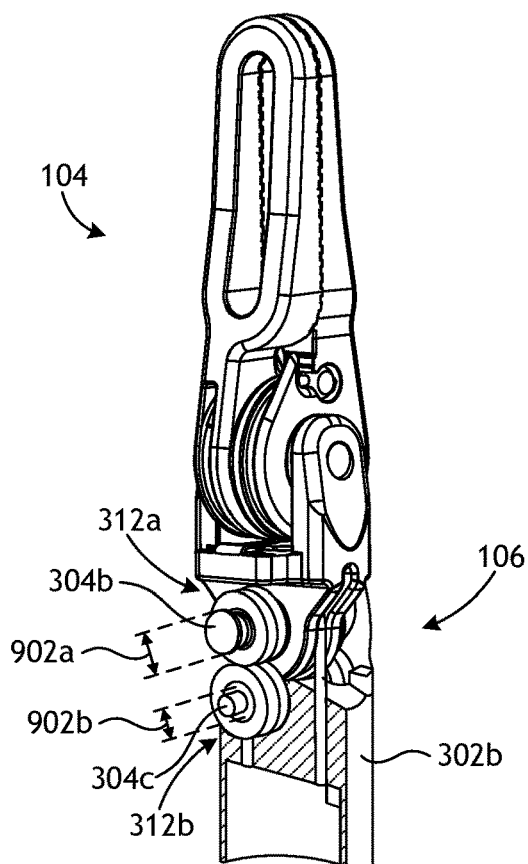
FIG. 9 is an isometric side view of the end effector and a portion of the wrist of FIGS. 3 and 4, according to one or more additional embodiments.

FIG. 9 is an isometric side view of the end effector 104 and a portion of the wrist 106 of FIGS. 3 and 4, according to one or more additional embodiments. The proximal clevis 302b is shown in cross-section to expose the first and second pluralities of pulleys 312a,b for discussion. As illustrated, the second axle 304b is larger than the third axle 304c, and the outer diameter of each of the pulleys 312a,b is substantially the same. However, because the second axle 304b is larger than the third axle 304c, an inner diameter 902b of the second plurality of pulleys 312b may be smaller than an inner diameter 902a of the first plurality of pulleys 312a.

As discussed above, the first and second pluralities of pulleys 312a,b cooperatively redirect the drive cables 308a-d (FIG. 3) through an "S" shaped pathway extending to and from the end effector 104. The smaller inner diameter 902b of the second plurality of pulleys 312b equates to less bend angle applied to the drive cables 308a-d as they are routed through the "S" shaped pathway. Less bend angle equates to less touching of the drive cables 308a-d against the second plurality of pulleys 312b, which advantageously reduces friction and inefficiencies on the third axle 304c during operation.

Figure 10:
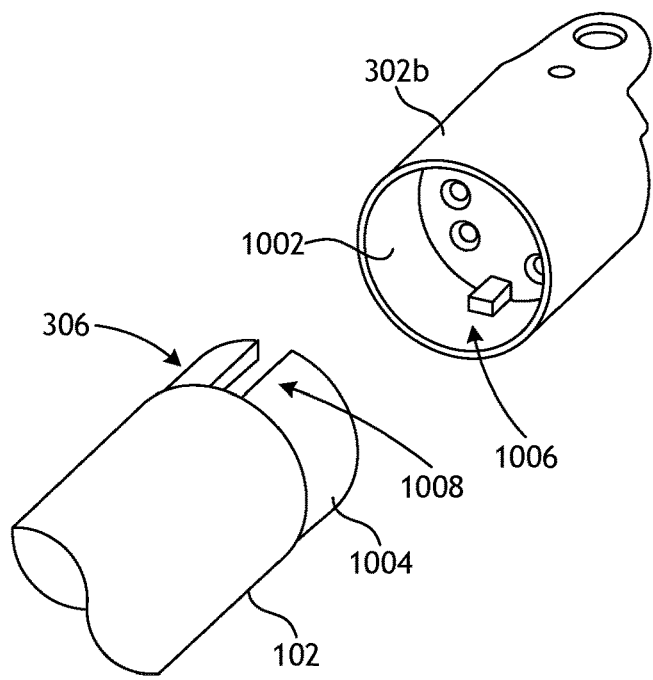
FIG. 10 is an exploded view of the proximal clevis and the distal portion of the elongate shaft.

FIG. 10 is an exploded view of the proximal clevis 302b and the distal end 306 of the elongate shaft 102, according to one or more embodiments. The proximal clevis 302b may be coupled to the distal end 306 of the shaft 102 in a variety of ways, without departing from the scope of the disclosure. Example ways that the proximal clevis 302b may be coupled to the distal end 306 of the shaft 102 include, but are not limited to, a threaded engagement, welding, brazing, an industrial adhesive, one or more mechanical fasteners, an interference fit (e.g., press fit, shrink fit, etc.), or any combination thereof.

In some embodiments, as illustrated, the proximal clevis 302b may be coupled to the distal end 306 of the shaft 102 by receiving the distal end 306 within an interior 1002 of the proximal clevis 302b. The distal end 306 of the shaft 102 may define an annular recess 1004 sized to be received within the interior 1002 of the proximal clevis 302b. In some embodiments, the annular recess 1004 may be received within the interior 1002 via an interference fit (e.g., press fit, shrink fit, etc.). The interference fit coupling may be enhanced through welding, brazing, or an adhesive.

In some embodiments, the distal end 306 of the shaft 102 may define one or more keyways 1008 (one shown and one hidden) and one or more corresponding keys 1006 (one shown and one hidden) may be provided within the interior 1002 of the proximal clevis 302b. When the distal end 306 is received within the interior 1002, the keyway(s) 1008 may be configured to align with and receive the key(s) 1006, which prevents rotation of the wrist 106 (FIG. 3) relative to the shaft 102. Moreover, mating the key(s) 1006 with the keyway(s) 1008 may prove advantageous in ensuring that the shaft 102 will only couple to the proximal clevis 302b in a predetermined manner angular orientation, which ensures that the wrist 106 will be aligned with the shaft 102 in a known configuration.

Figure 11:
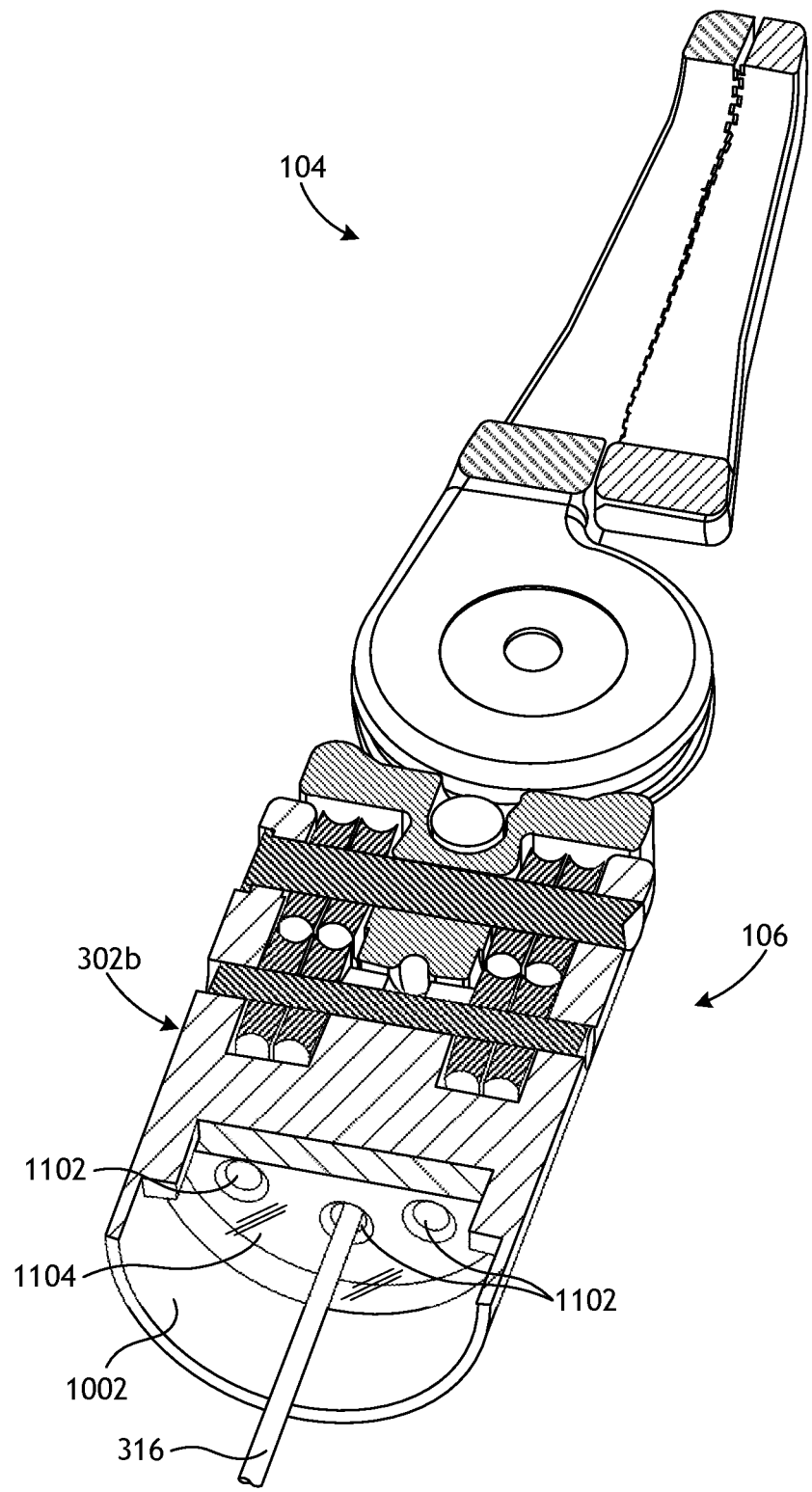
FIG. 11 is an isometric cross-sectional view of the end effector and the wrist, according to one or more additional embodiments.

FIG. 11 is an isometric cross-sectional view of the end effector 104 and the wrist 106, according to one or more additional embodiments. More specifically, a view of the interior 1002 of the proximal clevis 302b is depicted. In some embodiments, the proximal clevis 302b may define a plurality of channels 1102 configured to receive the drive cables 308a-d (FIG. 3) and the power axle cable 316. Accordingly, while only three channels 1102 are depicted in FIG. 11, the number of channels 1102 will generally be equal to the total number of drive cables 308a-d and the two ends of the power axle cable 316.

In some embodiments, a seal 1104 may be provided within the interior 1002 of the proximal clevis 302b. In at least one embodiment, the seal 1104 may comprise a silicone seal and the drive cables 308a-d (FIG. 3) and the power axle cable 316 may pass through the seal 1104 with little or no friction generation. The seal 1104 may prove advantageous in helping to maintain insufflation during surgical operations, and may also provide a barrier that helps prevent debris, blood, and other matter from getting into the shaft 102 (FIGS. 3 and 10) and other parts of a surgical tool.

Embodiments disclosed herein include:

A surgical tool that includes a drive housing, an elongate shaft that extends from the drive housing, a wrist that couples an end effector to the elongate shaft and includes a distal clevis having a first axle that rotatably mounts the end effector to the distal clevis, and a proximal clevis coupled to a distal end of the elongate shaft and having a second axle that rotatably mounts the distal clevis to the proximal clevis, a plurality of drive cables extending between the drive housing and the end effector, wherein movement of one or more of the plurality of drive cables causes the end effector to articulate about a first pivot axis extending through the first axle, and a power axle cable extending from the drive housing and mounted to the distal clevis such that movement of the power axle cable correspondingly pivots the end effector about a second pivot axis extending through the second axle and perpendicular to the first pivot axis.

B. A method of operating a surgical tool that includes positioning the surgical tool adjacent a patient for operation, the surgical tool including a drive housing, an elongate shaft that extends from the drive housing, a wrist that couples an end effector to the elongate shaft and includes a distal clevis having a first axle that rotatably mounts the end effector to the distal clevis, and a proximal clevis coupled to a distal end of the elongate shaft and having a second axle that rotatably mounts the distal clevis to the proximal clevis, a plurality of drive cables extending between the drive housing and the end effector, and a power axle cable extending from the drive housing and mounted to the distal clevis. The method further including moving one or more of the plurality of drive cables and thereby causing the end effector to articulate about a first pivot axis extending through the first axle, and moving the power axle cable and thereby pivoting the end effector about a second pivot axis extending through the second axle and perpendicular to the first pivot axis.

C. A power axle wrist for a surgical tool that couples an end effector to an elongate shaft of the surgical tool, the power axle wrist including a distal clevis having a first axle where the end effector is rotatably mounted to the distal clevis, the end effector being articulable about a first pivot axis extending through the first axle, a proximal clevis configured to be coupled to a distal end of the elongate shaft and having a second axle where the distal clevis is rotatably mounted to the proximal clevis, and a power axle cable mounted to the distal clevis such that movement of the power axle cable correspondingly pivots the end effector about a second pivot axis extending through the second axle and perpendicular to the first pivot axis.

Each of embodiments A, B, and C may have one or more of the following additional elements in any combination: Element 1: wherein the wrist further includes a pocket defined in the distal clevis and sized to receive a power axle connector secured to the power axle cable, and an inner pulley provided by the distal clevis and defining an inner groove that concentrically circumscribes the second axle, wherein the power axle cable is received within the inner groove. Element 2: wherein a portion of the power axle connector protrudes out of the pocket and a recess is defined on the end effector to accommodate the portion of the power axle connector such that the power axle connector does not obstruct movement of the end effector about the first pivot axis. Element 3: wherein the wrist further includes a first plurality of pulleys mounted to the proximal clevis at the second axle, and a second plurality of pulleys mounted to the proximal clevis at a third axle located proximal to the second axle, and wherein the first and second plurality of pulleys cooperatively redirect the plurality of drive cables through an "S" shaped pathway while the power axle cable is routed directly to the distal clevis. Element 4: wherein an outer diameter of each pulley of the first and second pluralities of pulleys is the same, but an inner diameter of each pulley of the second plurality of pulleys is smaller than an inner diameter of each pulley of the first plurality of pulleys. Element 5: wherein the end effector includes opposing first and second jaws, and wherein movement of the plurality of drive cables causes one or both of the first and second jaws to pivot about the first pivot axis in yaw articulation and movement of the power axle cable causes movement of the end effector about the second pivot axis in pitch articulation. Element 6: wherein the plurality of drive cables include a first pair of drive cables coupled at a first connector mounted to the first jaw in a first pocket and a second pair of drive cables coupled at a second connector mounted to the second jaw in a second pocket, and wherein a nose extends from each jaw to maintain the first and second connectors within the first and second pockets, respectively. Element 7: wherein the distal clevis provides at least one hard stop positioned to limit the yaw articulation of at least one of the first and second jaws to a predetermined maximum angle. Element 8: wherein a distal end of the elongate shaft is received within an interior of the proximal clevis, and the distal end of the elongate shaft defines one or more keyways mateable with one or more corresponding keys provided within the interior of the proximal clevis. Element 9: wherein the distal clevis provides a plurality of channels and each drive cable extends proximally from the end effector and passes through a corresponding one of the plurality of channels without touching the corresponding one of the plurality of channels. Element 10: wherein the end effector is selected from the group consisting of forceps, a tissue grasper, a needle driver, scissors, an electro cautery tool, a stapler, a clip applier, a suction tool, an irrigation tool, an imaging device, a babcock, a retractor, a hook, a spatula, and any combination thereof.

Element 11: wherein the end effector includes opposing first and second jaws, and wherein moving the one or more of the plurality of drive cables comprises causing one or both of the first and second jaws to pivot about the first pivot axis in yaw articulation, and wherein moving the power axle cable comprises causing movement of the end effector about the second pivot axis in pitch articulation. Element 12: further comprising helping to maintain insufflation with a seal provided within an interior of the proximal clevis.

Element 13: further comprising a pocket defined in the distal clevis and sized to receive a power axle connector secured to the power axle cable, and an inner pulley provided by the distal clevis and defining an inner groove that concentrically circumscribes the second axle, wherein the power axle cable is received within the inner groove. Element 14: wherein the power axle connector comprises an attachment mechanism selected from the group consisting of a crimp, a welded attachment, a brazed attachment, an adhesive bond, a mechanical fastener, and any combination thereof. Element 15: further comprising a first plurality of pulleys mounted to the second axle, a second plurality of pulleys mounted to a third axle coupled to the proximal clevis and located proximal to the second axle, wherein an outer diameter of each pulley of the first and second pluralities of pulleys is the same, but an inner diameter of each pulley of the second plurality of pulleys is smaller than an inner diameter of each pulley of the first plurality of pulleys. Element 16: wherein the distal clevis provides a first extension that defines a first hole having a first inner diameter, and a second extension laterally offset from the first extension and defining a second hole having a second inner diameter greater than the first inner diameter, and wherein the first axle is extendable through the first and second holes and provides a first end with a first outer diameter similar to the first inner diameter, and a second end with a second outer diameter similar to the second inner diameter. Element 17: further comprising a seal provided within an interior of the proximal clevis.

By way of non-limiting example, exemplary combinations applicable to A, B, and C include: Element 1 with Element 2; Element 3 with Element 4; Element 5 with Element 6; Element 5 with Element 7; and Element 13 with Element 14.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
   a drive housing;
   an elongate shaft that extends from the drive housing;
   a wrist that couples an end effector to the elongate shaft and includes a distal clevis that defines an inner pulley and has a first axle that rotatably mounts the end effector to the distal clevis, and a proximal clevis coupled to a distal end of the elongate shaft and having a second axle that rotatably mounts the distal clevis to the proximal clevis;
   a plurality of drive cables extending between the drive housing and the end effector, wherein movement of one or more of the plurality of drive cables causes the end effector to articulate about a first pivot axis extending through the first axle; and
   a power axle cable extending from the drive housing and mounted to the distal clevis at the inner pulley,
   wherein a power axle connector is secured to the power axle cable and received within a pocket defined in the distal clevis such that movement of the power axle cable correspondingly pivots the end effector about a second pivot axis extending through the second axle and perpendicular to the first pivot axis, and
   wherein a portion of the power axle connector protrudes from the pocket and a recess is defined on the end effector to accommodate the portion of the power axle connector such that the power axle connector does not obstruct movement of the end effector about the first pivot axis.

2. The surgical tool of claim 1, wherein the inner groove that concentrically circumscribes the second axle and the power axle cable is received within the inner groove.

3. The surgical tool of claim 1, wherein the wrist further includes a first plurality of pulleys mounted to the proximal clevis at the second axle, and a second plurality of pulleys mounted to the proximal clevis at a third axle located proximal to the second axle, and
   wherein the first and second plurality of pulleys cooperatively redirect the plurality of drive cables through an "S" shaped pathway while the power axle cable is routed directly to the distal clevis.

4. The surgical tool of claim 3, wherein an outer diameter of each pulley of the first and second pluralities of pulleys is the same, but an inner diameter of each pulley of the second plurality of pulleys is smaller than an inner diameter of each pulley of the first plurality of pulleys.

5. The surgical tool of claim 1, wherein the end effector includes opposing first and second jaws, and wherein movement of the plurality of drive cables causes one or both of the first and second jaws to pivot about the first pivot axis in yaw articulation and movement of the power axle cable causes movement of the end effector about the second pivot axis in pitch articulation.

6. The surgical tool of claim 5, wherein the plurality of drive cables include a first pair of drive cables coupled at a first connector mounted to the first jaw in a first pocket and a second pair of drive cables coupled at a second connector mounted to the second jaw in a second pocket, and wherein a nose extends from each jaw to maintain the first and second connectors within the first and second pockets, respectively.

7. The surgical tool of claim 5, wherein the distal clevis provides at least one hard stop positioned to limit the yaw articulation of at least one of the first and second jaws to a predetermined maximum angle.

8. The surgical tool of claim 1, wherein a distal end of the elongate shaft is received within an interior of the proximal clevis, and the distal end of the elongate shaft defines one or more keyways mateable with one or more corresponding keys provided within the interior of the proximal clevis.

9. The surgical tool of claim 1, wherein the distal clevis provides a plurality of channels and each drive cable extends proximally from the end effector and passes through a corresponding one of the plurality of channels without touching the corresponding one of the plurality of channels.

10. The surgical tool of claim 1, wherein the end effector is selected from the group consisting of forceps, a tissue grasper, a needle driver, scissors, an electro cautery tool, a stapler, a clip applier, a suction tool, an irrigation tool, an imaging device, a babcock, a retractor, a hook, a spatula, and any combination thereof.

11. A power axle wrist for a surgical tool that couples an end effector to an elongate shaft of the surgical tool, the power axle wrist comprising:
a distal clevis having a first axle where the end effector is rotatably mounted to the distal clevis, the end effector being articulable about a first pivot axis extending through the first axle;
a proximal clevis configured to be coupled to a distal end of the elongate shaft and having a second axle where the distal clevis is rotatably mounted to the proximal clevis;
a power axle cable mounted to the distal clevis at an inner pulley, the proximal clevis defining a plurality of channels through which a plurality of drive cables and the power axle cable extend; and
a power axle connector secured to the power axle cable and received within a pocket defined in the distal clevis such that movement of the power axle cable correspondingly pivots the end effector about a second pivot axis extending through the second axle and perpendicular to the first pivot axis,
wherein a portion of the power axle connector protrudes from the pocket and a recess is defined on the end effector to accommodate the portion of the power axle connector such that the power axle connector does not obstruct movement of the end effector about the first pivot axis.

12. The power axle wrist of claim 11, wherein the inner pulley defines an inner groove that concentrically circumscribes the second axle and the power axle cable is received within the inner groove.

13. The power axle wrist of claim 12, wherein the power axle connector comprises an attachment mechanism selected from the group consisting of a crimp, a welded attachment, a brazed attachment, an adhesive bond, a mechanical fastener, and any combination thereof.

14. The power axle wrist of claim 11, further comprising:
a first plurality of pulleys mounted to the second axle;
a second plurality of pulleys mounted to a third axle coupled to the proximal clevis and located proximal to the second axle,
wherein an outer diameter of each pulley of the first and second pluralities of pulleys is the same, but an inner diameter of each pulley of the second plurality of pulleys is smaller than an inner diameter of each pulley of the first plurality of pulleys.

15. The power axle wrist of claim 11, wherein the distal clevis provides a first extension that defines a first hole having a first inner diameter, and a second extension laterally offset from the first extension and defining a second hole having a second inner diameter greater than the first inner diameter, and
wherein the first axle is extendable through the first and second holes and provides a first end with a first outer diameter similar to the first inner diameter, and a second end with a second outer diameter similar to the second inner diameter.

16. The power axle wrist of claim 11, wherein the power axle further comprising a seal provided within an interior of the proximal clevis adjacent the plurality of channels, wherein the plurality of drive cables and the power axle cable extend through the seal.

17. A method of operating a surgical tool, comprising:
positioning the surgical tool adjacent a patient for operation, the surgical tool including:
a drive housing;
an elongate shaft extending from the drive housing;
a wrist that couples an end effector to the elongate shaft and includes a distal clevis that defines an inner pulley and has a first axle that rotatably mounts the end effector to the distal clevis, and a proximal clevis coupled to a distal end of the elongate shaft and having a second axle that rotatably mounts the distal clevis to the proximal clevis;
a plurality of drive cables extending between the drive housing and the end effector; and
a power axle cable extending from the drive housing and mounted to the distal clevis at the inner pulley, wherein a power axle connector is secured to the power axle cable and received within a pocket defined in the distal clevis;
moving one or more of the plurality of drive cables to articulate the end effector about a first pivot axis extending through the first axle; and
moving the power axle cable and thereby pivoting the end effector about a second pivot axis extending through the second axle and perpendicular to the first pivot axis,
wherein a portion of the power axle connector protrudes from the pocket and a recess is defined on the end effector to accommodate the portion of the power axle connector such that the power axle connector does not obstruct movement of the end effector about the first pivot axis.

18. The method of claim 17, wherein the end effector includes opposing first and second jaws, and
wherein moving the one or more of the plurality of drive cables comprises causing one or both of the first and second jaws to pivot about the first pivot axis in yaw articulation, and
wherein moving the power axle cable comprises causing movement of the end effector about the second pivot axis in pitch articulation.

19. The method of claim 17, further comprising helping to maintain insufflation with a seal provided within an interior of the proximal clevis.

* * * * *